(12) United States Patent
Zhan et al.

(10) Patent No.: US 8,540,960 B2
(45) Date of Patent: Sep. 24, 2013

(54) METHOD FOR PRODUCING OF ULTRA-CLEAN AND HIGH-PURITY ELECTRONIC GRADE REAGENTS

(75) Inventors: Jiarong Zhan, Putuo Shanghai (CN);
Mao Huiping, Putuo Shanghai (CN);
Hui Shaoliang, Putuo Shanghai (CN);
Shen Zheyu, Putuo Shanghai (CN)

(73) Assignee: Shanghai Chemical Reagent Research Institute, Shanghai (CN)

( * ) Notice: Subject to any disclaimer, the term of this patent is extended or adjusted under 35 U.S.C. 154(b) by 344 days.

(21) Appl. No.: 12/914,716

(22) Filed: Oct. 28, 2010

(65) Prior Publication Data

US 2011/0094872 A1    Apr. 28, 2011

(30) Foreign Application Priority Data

Sep. 16, 2010  (CN) .......................... 2010 1 0282669

(51) Int. Cl.
| | | |
|---|---|---|
| *C01B 7/07* | (2006.01) | |
| *B01D 46/00* | (2006.01) | |
| *B01D 3/26* | (2006.01) | |
| *C07C 29/80* | (2006.01) | |
| *C07C 31/10* | (2006.01) | |

(52) U.S. Cl.
USPC ........ 423/488; 159/DIG. 27; 203/18; 203/40; 210/295; 210/640; 210/650; 210/749; 568/889; 568/916

(58) Field of Classification Search
USPC .................... 159/DIG. 27; 203/6, 18, 40, 49, 203/96; 210/295, 640, 650, 749; 423/488; 568/889, 916
See application file for complete search history.

(56) References Cited

U.S. PATENT DOCUMENTS

| | | | | |
|---|---|---|---|---|
| 3,750,735 | A * | 8/1973 | Chiang et al. ................... | 159/49 |
| 4,170,551 | A * | 10/1979 | Honour ........................ | 122/446 |
| 4,788,043 | A * | 11/1988 | Kagiyama et al. ............ | 422/292 |
| 4,879,041 | A * | 11/1989 | Kurokawa et al. ............ | 210/640 |
| 4,953,694 | A * | 9/1990 | Hayashi et al. ............... | 202/180 |
| 5,585,527 | A * | 12/1996 | Marker .......................... | 203/18 |
| 5,868,906 | A * | 2/1999 | Adams et al. ................. | 203/18 |
| 6,733,637 | B1 * | 5/2004 | Burton et al. ................. | 203/14 |
| 8,075,740 | B2 * | 12/2011 | Bailie et al. .................. | 202/176 |

* cited by examiner

*Primary Examiner* — Virginia Manoharan
(74) *Attorney, Agent, or Firm* — Nath, Goldberg & Meyer; Joshua B. Goldberg; Megan B. Doughty

(57) ABSTRACT

A method for producing of ultra-clean and High-purity electronic grade reagents is disclosed. The industrial grade reagents are chemically pretreated and filtered, and the colature is rectified. Heating the steam during the rectification to overheated steam, and filtering the overheated steam used the microporous membrane to remove the solid particulates. Condensing the overheated steam and the secondarily filter to remove the dust in the product. Due to the adoption of the technical scheme, the ultra-clean and High-purity isopropanol produced is in conformity with standard SEMI-C12 and the hydrochloric acid to standard SEMI-C8. And the method is applicable for the large-scale continuous production.

6 Claims, 1 Drawing Sheet

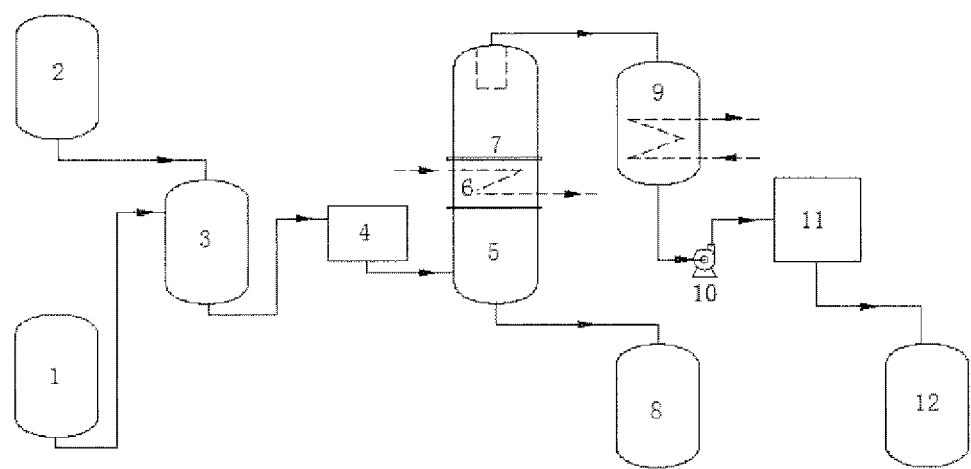

METHOD FOR PRODUCING OF ULTRA-CLEAN AND HIGH-PURITY ELECTRONIC GRADE REAGENTS

FIELD OF THE INVENTION

The present invention relates to a method for producing electronic grade reagents, in particular, it relates to a method for producing ultra-clean and high-purity electronic grade isopropanol and hydrochloric acid.

BACKGROUND OF THE INVENTION

The ultra-clean and high-purity reagents (also called Process Chemicals or Wet Chemicals) are important and basic materials in the production of Very Large-Scale Integration (VLSI). Both ultra-clean and high-purity electronic grade isopropanol and hydrochloric acid are very important and extensively used in producing semiconductors and cleaning corrosion during the assemblage of very large-scale integration etc.

Because of the rapid development of IT technology, the purity requirement of Process Chemicals is higher and higher. Particularly, with the integrated circuit's development and trends towards miniaturization and high speed processing, the requirement of purity is more critical than before. The content of single cation of the electronic grade hydrochloric acid or isopropanol turns into the ppb level from the ppm level, and correspondingly, the standard of the electronic grade hydrochloric acid and isopropanol turns into SEMI-C8 or SEMI-C12 from SEMI-C1 and SEMI-C7 (The SEMI-C is the chemical standard published by Semiconductor Equipment and Material International).

The regular production of liquid Process Chemicals such as hydrochloric acid and isopropanol comprises sub-boiling distillation that uses thermal radiation to hold the liquid phase temperature lower than boiling point and then evaporating and condensing to produce reagents, or rectification. But there is not mature technology for large-scale sub-boiling distillation production, and the concentration of impurities in the electronic grade hydrochloric acid and isopropanol produced with regular rectification is high.

"PURE AND APPLIED CHEMISTRY" (1986, (10): 1412-1418) disclosed a method for the production of ultra-clean and high-purity isopropanol. Adding CaO or Mg powder to reflux with iodine as an activator, and then multiple rectifying to get a product of 99.4% purity and a moisture content of 600 ppm. However, the moisture content of the isopropanol produced through this method is too high.

Bin Zhu etc. reported a method for producing electronic grade isopropanol in "Continuous Production of Electronic Grade Isopropanol from Technical Grade Isopropanol" (*NATURAL GAS CHEMICAL INDUSTRY,* 2009, 34(2): 67). The continuous production of electronic grade isopropanol is realized through the combination of sub-boiling rectification and batch rectification. The product is in conformity with the CEMI-C8 standard, but the yield is reduced.

Chinese patent No. CN101362675A disclosed a method for the production of ultra-clean and high-purity isopropanol. Industrial grade isopropanol is purified through four-stage rectification. The method of multistage rectification is high risk and requires heavy energy consumption.

Chinese patent No. CN1644487A disclosed a device with which the ultra-clean and high-purity hydrochloric acid can be produced with low temperature evaporation. The hydrochloride passes through two-stage washing columns and bubbling columns and is absorbed by conductivity water in an absorption tower. Then, it is evaporated at a low temperature and finely filtered to produce electronic grade hydrochloric acid. We can see that the equipments used in this invention are complicated.

Chinese patent No. CN1326766C disclosed a method for producing electronic grade hydrochloric acid. The hydrochloride acid produced can be used only as MOS grade or BV-III standard reagent in production of VLSI because of its limited purity.

DESCRIPTION OF THE INVENTION

The present invention provides a method for producing ultra-clean and high-purity reagents with industrial grade hydrochloric acid or isopropanol as crude material. The hydrochloric acid or isopropanol meeting the SEMI-C8 or SEMI-C12 standard is produced in high yield and quality by the combination of overheated steam, a microporous membrane filtration and rectification. Additionally, the present invention overcomes the defects of high impurity content brought by traditional methods.

The method for producing ultra-clean and high-purity electronic grade reagents includes the following steps:

Step 1, under room temperature, the industrial grade isopropanol or hydrochloric acid is chemically pretreated and filtered; and a colature is collected;

Step 2, rectifying the colature and heating the steam to produce overheated steam during the rectification, and then filtering the overheated steam through the microporous membrane;

Step 3, condensing the overheated steam, secondarily filtering the fraction collected through the microporous membrane, and controlling the number of solid particle to get the ultra-clean and High-purity isopropanol or hydrochloric acid.

The aperture of the microporous membrane, which is usually 0.1~0.5 μm, can be determined according to the content of the impurity, and the microporous membrane can be composed of membrane and supporting frame, both made of perfluoro-polymer.

It is not necessary that the temperature of the overheated steam be too high; merely 2~10° C. higher than the temperature of the steam in the rectifying column is sufficient.

It would be better to control the flow rate of the steam to 0.5~1.5 m/s during the rectification.

An embodiment of the present invention includes following steps:

Step 1, adding the dearsenical agent to industrial grade hydrochloric acid, reacting 0.5~1.5 hours to remove arsenic; filtering the hydrochloric acid and collecting the colature;

Step 2, under the temperature of 115~116° C. in the top part of the rectifying column, atmospherically rectifying the colature with the flow rate of 0.5~1.5 meter/second in the column, and heating the steam to 118~120° C. to produce overheated steam during the rectification; then filtering the overheated steam through the microporous membrane of 0.1 μm aperture;

Step 3, condensing the overheated steam and collecting the fraction, and secondarily filtering the fraction through the microporous membrane.

The optimal dearsenical agent used is hydrazine hydrate in a mass concentration of 40%.

The optimal weight ratio between the hydrazine hydrate and the industrial grade hydrochloric acid is 5~8:100.

Another embodiment of the present invention includes following steps:

Step 1, adding the dehydrant to the industrial grade isopropanol to react for 0.5~1.5 hours, filtering the isopropanol and collecting the colature;

Step 2, under the temperature of 82~83° C. in the top part of the rectifying column, atmospherically rectifying the colature with the flow rate of 0.5~1.5 m/s in the column, and heating the steam to 84~86° C. to produce overheated steam during the rectification; then filtering the overheated steam through the microporous membrane with 0.1 μm aperture;

Step 3, condensing the overheated steam and collecting the fraction, and secondarily filtering the fraction through the microporous membrane.

The optimal dehydrant used is the $CaCl_2$.

The optimal weight ratio between the $CaCl_2$ and the industrial grade isopropanol is 3~5:100.

In the above methods, the caskets and pipe walls in contact with the isopropanol or hydrochloric acid preferably is made of the high-purity quartz or perfluoro-polymer. Additionally, the reservoirs preferably are made of perfluoro-polymer.

The ultra-clean and high-purity isopropanol produced has a purity higher than 99.80%. In addition, the ultra-clean and high-purity isopropanol produced has a single cation content lower than 0.1 ppb and a particulate content of ≥0.2 μm, which is lower than 5 pcs/ml. This is in conformity with the SEMI-C12 standard.

The ultra-clean and high-purity hydrochloric acid produced has a qualified purity. In addition, the ultra-clean and high-purity hydrochloric acid produced has a single cation content lower than 1.0 ppb and a particulate content of ≥0.5 μm, which is lower than 10 pcs/ml. This is in conformity with the SEMI-C8 standard.

Overheated steam is involved in the method of the present invention. The steam and priming in the top half of the rectifying column is heated to a higher temperature than the boiling point of the feed liquor to produce overheated steam. The priming is eliminated so only the steam and solid particulates made by ions persist. The particulates and ions can be removed by twice filtrations. So the present invention overcomes the defect of high impurity content brought by traditional methods. The yield increases 0.5~1 time, and the steam is cut per consumption in more than half. Additionally, the method is applicable for large-scale continuous production.

BRIEF DESCRIPTION OF THE DRAWINGS

FIG. 1 illustrates the process of the method of the present invention.

DETAILED DESCRIPTION OF THE PREFERRED EMBODIMENTS

A better understanding of the present invention is obtained when the following non-limiting detailed description is considered with rectifying column as in FIG. 1. In FIG. 1, sign 1 is industrial grade materials; sign 2 is pretreated agents; sign 3 is pretreatment reactor; sign 4 is filter; sign 5 is rectifying column; sign 6 is heater; sign 7 is the microporous membrane filter; sign 8 is by-product recovery unit; sign 9 is cooling column; sign 10 is pump; sign 11 is the secondary microporous membrane filter; sign 12 is reservoir.

Step 1: under the normal temperature, industrial hydrochloric acid or isopropanol and pretreated agents such as dehydrant, dearsenical agent, oxidant or reductant are fed into the pretreatment reactor for pretreatment reaction to remove impurities and increase purity.

Then, the crude material is filtered and the colature is collected.

Step 2: Rectifying the colature in the rectifying column with 0.5~1.5 m/s flow rate of the steam.

There is a heater in the rectifying column to heat the steam during the rectification to produce overheated steam. Additionally, there is a microporous membrane filter in the top half of rectifying column to filter the overheated steam.

The most important part of the microporous membrane filter is the microporous membrane that is formed by a membrane and a supporting frame, both of which are made of perfluoro-polymer (that is, the polymer where all hydrogen atoms linked with carbon atoms are replaced by fluorine atoms such as the polytetrafluoroethylene or the tetrafluoroethylene-hexaluoropropylene copolymer). The perfluoropolymer can be used when producing almost all reagents because of its supernormal stability and wide range of usage temperature. Additionally, the aperture of the microporous membrane, usually 0.1~0.5 μm, can be determined according to the content of the impurity.

Because of some priming generated during rectification and some impurities interfused in the priming, there will be some impurities in the fraction and the purity of the product will be low. The overheated steam can gasify the priming to remove the priming in the steam. However, the temperature of the overheated steam does not have to be too high; 2~10° C. higher than the temperature of the steam in the rectifying column is sufficient. The reason is that the thermal energy will be wasted and the useful life of the membrane will be shortened if the temperature of the overheated steam is too high.

Step 3: Condensing the overheated steam passed through the microporous membrane filter and collecting the fraction. The fraction is pumped into the secondary microporous membrane filter to remove the particulates. The product is stored in a reservoir and the by-product generated during the rectification is stored in a by-product recovery unit.

In the methods above, the caskets and pipe walls in contact with isopropanol or hydrochloric acid preferably is made of high-purity quartz or perfluoro-polymer. Additionally, the reservoirs preferably are made of perfluoro-polymer.

The purity is detected through the following methods: Optical Colorimetry with Platinum-Cobalt Standard Solution is chosen as the standard color for chromaticity; Gas Chromatography is applied in the Analysis for the content of isopropanol or hydrochloride; Carl Fisher Method is applied for the water content; Gravimetric Analysis is used for the residue after evaporation; ICP-MS is applied for the cations; and Ion-exchange Chromatograph Analysis is used for the anions.

The analytical instruments are list in table1.

TABLE 1

Analytical Instruments

| Title | Technical requirement | Type |
|---|---|---|
| Autotitrator | <0.01% | Mettler DL50 |
| ICP-MS | detection limit <1 ppt | Agilent ICP-MS-7500S |
| Moisture Titrator | DL31 | METTLER TOLEDO |
| Double-pump Liquid Chromatograph | 1525 | Waters |
| Turbidity Meter | detection limit <1 ppb | 2100N HACH |
| Ultraviolet Spectrophotometer | anion <20 ppb | Thermal Alpha UV-Vis |
| Laser Light Scattering Particle Detector | content particles of <0.1 μm diameter | Rion 40AF |

Embodiment 1

$CaCl_2$ is added into industrial isopropanol of 99.0 wt % and reacted for 0.5~1 hours for dehydration. The weight ratio between the $CaCl_2$ and the industrial isopropanol is 3~5:100. Then, the isopropanol is filtered and the colature is collected.

The colature is rectified at a temperature of 82~83° C. in the top part of the rectifying column and the normal atmosphere with the 0.5 m/s flow rate of the steam. The steam is heated to produce overheated steam of 84~86° C. The overheated steam is filtered by the microporous membrane filter with 0.1 μm aperture and condensed to liquid to remove the particles impurities.

The fraction is filtered through the secondary microporous membrane filter to remove most impurities and get ultra-clean and high-purity isopropanol. The purity of the product is 99.85%, the content of single cations is lower than 0.1 ppb, the content of the particulates, which are larger than 0.2 μm in diameter, is lower than 5 pcs/ml, and the product is in conformity with the SEMI-C12 standard.

Embodiment 2

$CaCl_2$ is added into industrial isopropanol of 99.0 wt % to dehydration. The isopropanol is filtered and the colature is collected.

The colature is rectified at a temperature of 82~83° C. in the top part of the rectifying column and the normal atmosphere. The flow rate of the steam is controlled to be 1.0 m/s to increase the production rate and productivity. The steam is heated to turn into the overheated steam of 84~86° C. The overheated steam is filtered by the microporous membrane filter of 0.1 μm aperture and condensed to liquid to remove the particles and impurities.

The fraction is filtered by the secondary microporous membrane filter to remove most impurities and get the ultra-clean and high-purity isopropanol. The purity of the product is 99.89%, the content of single cations is lower than 0.1 ppb, the content of the particulates of ≥0.2 μm is lower than 5 pcs/ml, and the product is in conformity with the SEMI-C12 standard.

The analytical results of the purity are list in table2.

TABLE 2 the analytical results of the purity

| Parameter | U.M. | SEMI-C12 | Embodiment 1 | Embodiment 2 |
|---|---|---|---|---|
| Color | APHA | 10 | 6 | 7 |
| Isopropanol | % | >99.80 | 99.85 | 99.89 |
| Water | ppm | <50 | 39 | 43 |
| Residue after evaporation | ppm | <1.0 | 0.6 | 0.7 |
| Chloride(Cl) | ppb | <50 | none | none |
| Nitrate($NO_3$) | ppb | <50 | 35 | 35 |
| Phosphate($PO_4$) | ppb | <50 | 30 | 35 |
| Sulfate($SO_4$) | ppb | <50 | 35 | 28 |
| Aluminum(Al) | ppb | <0.1 | 0.05 | 0.07 |
| Arsenic(As) | ppb | <0.1 | 0.07 | 0.05 |
| Barium(Ba) | ppb | <0.1 | 0.09 | 0.08 |
| Boron(B) | ppb | <0.1 | 0.06 | 0.06 |
| Calcium(Ca) | ppb | <0.1 | 0.07 | 0.08 |
| Copper(Cu) | ppb | <0.1 | 0.07 | 0.06 |
| Iron(Fe) | ppb | <0.1 | 0.09 | 0.09 |
| Lead(Pb) | ppb | <0.1 | 0.05 | 0.06 |
| Magnesium(Mg) | ppb | <0.1 | 0.05 | 0.06 |
| Manganese(Mn) | ppb | <0.1 | none | none |
| Nickel(Ni) | ppb | <0.1 | none | none |
| Potassium(K) | ppb | <0.1 | 0.08 | 0.08 |
| Sodium(Na) | ppb | <0.1 | 0.09 | 0.07 |
| Tin(Sn) | ppb | <0.1 | none | none |
| Titanium(Ti) | ppb | <0.1 | none | none |
| Zinc(Zn) | ppb | <0.1 | 0.05 | 0.06 |
| ≥0.5 μm particulate | pcs/ml | ≤20 | 4 | 3 |

Embodiment 3

The hydrazine hydrate of 40% mass concentration is added into industrial hydrochloric acid of 30.0 wt % and reacted for 0.5~1 hours for dearsenization. The weight ratio between the hydrazine hydrate and the industrial hydrochloric acid is 5~8:100. The isopropanol is filtered and the colature is collected.

The colature is rectified at a temperature of 115~116° C. in the top part of the rectifying column and the normal atmosphere with the 0.5 m/s flow rate of the steam. The steam is heated to turn into overheated steam of 118~120° C. The overheated steam is filtered by the microporous membrane filter of 0.1 μm aperture and condensed to liquid to remove the particles and impurities.

The fraction is filtered by the secondary microporous membrane filter to remove most impurities and get ultra-clean and high-purity hydrochloric acid. The content of the hydrochloride is 36.2%, the content of single cations is lower than 1.0 ppb, the content of the particulates of ≥0.5 μm is 9 pcs/ml, and the product is in conformity with the SEMI-C8 standard.

The analytical results of the purity are list in table2.

TABLE 2 the analytical results of the purity

| Parameter | U.M. | SEMI-C8 | Embodiment 3 |
|---|---|---|---|
| Hydrochloride | wt % | 36.0 | 36.2 |
| Color | APHA | 10 | 6 |
| Free chlorine(as $Cl_2$) | tested | tested | tested |
| Extractable organic | ppm | 3 | 1 |
| Sulfate($SO_4$) | ppm | 0.2 | 0.13 |
| Phosphate($PO_4$) | ppm | 0.03 | 0.02 |
| Sulfite($SO_3$) | ppm | 0.7 | 0.5 |
| Aluminum(Al) | ppb | 3 | 2 |
| Antimony(Sb) | ppb | 1 | 0.7 |
| Arsenic(As) | ppb | 1 | 0.8 |
| Barium(Ba) | ppb | 1 | 0.5 |
| Beryllium(Be) | ppb | 1 | 0.4 |
| Bismuth(Bi) | ppb | 1 | 0.3 |
| Boron(B) | ppb | 3 | 1.0 |
| Cadmium(Cd) | ppb | 1 | 0.6 |
| Calcium(Ca) | ppb | 3 | 1.0 |
| Chromium(Cr) | ppb | 2 | 1.0 |
| Cobalt(Co) | ppb | 1 | 0.7 |
| Copper(Cu) | ppb | 1 | 0.6 |
| Gallium(Ga) | ppb | 1 | 0.5 |
| Germanium(Ge) | ppb | 1 | 0.4 |
| Gold(Au) | ppb | 1 | 0.3 |
| Iron(Fe) | ppb | 3 | 0.8 |
| Lead(Pb) | ppb | 1 | 0.7 |
| Lithium(Li) | ppb | 1 | 0.5 |
| Magnesium(Mg) | ppb | 1 | 0.6 |
| Manganese(Mn) | ppb | 1 | 0.7 |
| Molybdenum(Mo) | ppb | 1 | 0.5 |
| Nickel(Ni) | ppb | 1 | 0.4 |
| Potassium(K) | ppb | 2 | 0.9 |
| Silicon(Si) | ppb | — | — |
| Silver(Ag) | ppb | 1 | 0.4 |
| Sodium(Na) | ppb | 3 | 0.1 |
| Strontium(Sr) | ppb | 1 | 0.8 |

TABLE 2-continued the analytical results of the purity

| Parameter | U.M. | SEMI-C8 | Embodiment 3 |
|---|---|---|---|
| Tantalum(Ta) | ppb | 1 | 0.7 |
| Thallium(Tl) | ppb | 1 | 0.4 |
| Tin(Sn) | ppb | 3 | 0.6 |
| Titanium(Ti) | ppb | 1 | 0.5 |
| Vanadium(V) | ppb | 1 | 0.7 |
| Zinc(Zn) | ppb | 3 | 1.0 |
| Zirconium(Zr) | ppb | 1 | 0.5 |
| ≥0.5 μm particulate | pcs/ml | ≤15 | 9 |

The description above provides illustrations of the reagents and any operation not mentioned falls within the normal and routine operations in this field of technology, which would be understood by a person having ordinary skill in the art.

It shall be understood that the description of the embodiments above is only the illustrations of application, and it does not limit the invention to the specific embodiments illustrated. Numerous other ways of carrying out the method provided by the present invention may be devised by those skilled in the art without departing from the scope of the invention, thus they are encompassed by the present invention. Therefore it should be understood that any identical change can be done without departing from the scope of the present invention.

The invention claimed is:

1. A method for producing ultra-clean and high-purity hydrochloric acid comprising the following steps:
   step 1: adding a dearsenical agent to industrial grade hydrochloric acid at room temperature and reacting for 0.5-1.5 hours to remove arsenic; filtering the hydrochloric acid and collecting a filtrate;
   step 2: atmospherically rectifying the filtrate at a temperature of 115-116° C. in a top part of a rectifying column with 0.5-1.5 meter/second gas flow rate in the column, and heating steam to 118-120° C. to produce overheated steam during the rectification; then filtering the overheated steam through a microporous membrane having 0.1 μm apertures; and
   step 3: condensing the overheated steam filtered in step 2 and collecting a fraction, and filtering the fraction through a microporous membrane.

2. The method according to claim 1, wherein the dearsenical agent is hydrazine hydrate of 40% mass concentration.

3. The method according to claim 2, wherein the weight ratio between the hydrazine hydrate and the industrial grade hydrochloric acid is 5-8:100.

4. A method of producing ultra-clean and high-purity isopropanol comprising the following steps:
   step 1: adding a dehydrant to industrial grade isopropanol at room temperature and reacting for 0.5-1.5 hours; filtering the isopropanol and collecting a filtrate;
   step 2: atmospherically rectifying the filtrate at a temperature of 82-83° C. in a top part of a rectifying column with 0.5-1.5 m/s gas flow rate in the column, and heating steam to 84-86° C. to produce overheated steam during the rectification; then filtering the overheated steam through a microporous membrane having 0.1 μm apertures; and
   step 3: condensing the overheated steam filtered in step 2 and collecting a fraction, and filtering the fraction through a microporous membrane.

5. The method according to claim 4, wherein the dehydrant is $CaCl_2$.

6. The method according to claim 5, wherein the weight ratio between the $CaCl_2$ and the industrial grade isopropanol is 3-5:100.

* * * * *